United States Patent [19]

Hamill et al.

[11] 4,054,564
[45] Oct. 18, 1977

[54] 7-(5-AMINO-5-CARBOXYVALERAMIDO)-7-METHOXYCEPHALOSPORANIC ACID

[75] Inventors: Robert L. Hamill, New Ross; Calvin E. Higgens; Marvin M. Hoehn, both of Indianapolis, all of Ind.

[73] Assignee: Eli Lilly and Company, Indianapolis, Ind.

[21] Appl. No.: 251,619

[22] Filed: May 8, 1972

Related U.S. Application Data

[60] Division of Ser. No. 60,556, Aug. 3, 1970, Pat. No. 3,719,563, which is a continuation-in-part of Ser. No. 847,923, Aug. 6, 1969, abandoned.

[51] Int. Cl.$^2$ .................. C07D 501/28; A61K 31/545
[52] U.S. Cl. ...................................... 544/21; 424/246
[58] Field of Search .................................... 260/243 C

[56] References Cited

U.S. PATENT DOCUMENTS

B 331,417  1/1975  Stabley et al. .................. 260/243 C

OTHER PUBLICATIONS

Hackh's Chemical Dictionary 4th ed. (1969) p. 595.

Primary Examiner—Nicholas S. Rizzo
Assistant Examiner—Diana G. Rivers
Attorney, Agent, or Firm—Kathleen R. S. Page; Everet F. Smith

[57] ABSTRACT

Antibiotic A16884 and its salts, having antibacterial and anthelmintic activity, prepared by fermentation of *Streptomyces lipmanii* NRRI 3584.

2 Claims, 1 Drawing Figure

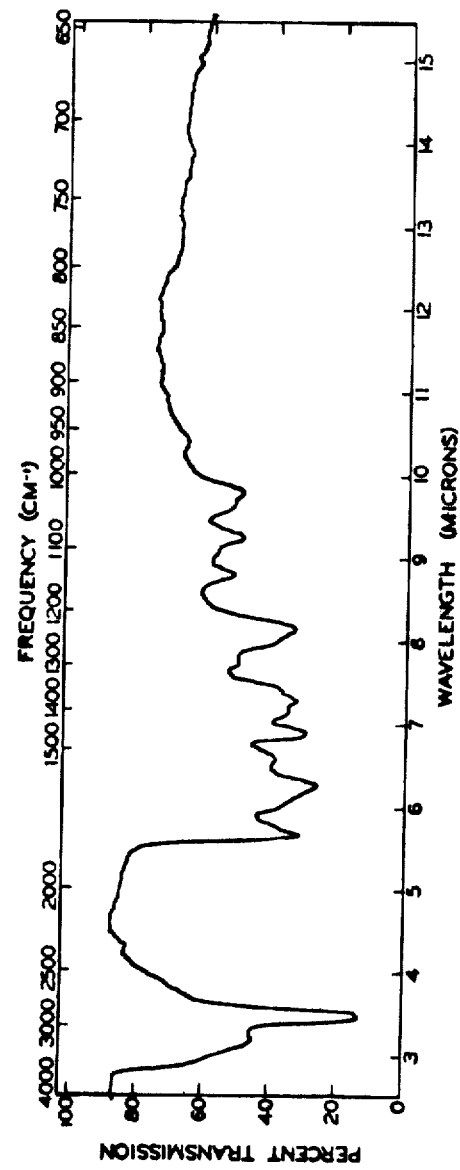

7-(5-AMINO-5-CARBOXYVALERAMIDO)-7-METHOXYCEPHALOSPORANIC ACID

CROSS-REFERENCE TO RELATED APPLICATIONS

This is a division of our co-pending application Ser. No. 60,556, filed Aug. 3, 1970, now U.S. Pat. No. 3,719,563, which was in turn a continuation-in-part of our then co-pending application Ser. No. 847,923, filed Aug. 6, 1969, and abandoned after the filing of said application Ser. No. 60,556.

SUMMARY OF THE INVENTION

Antibiotic A16884 is a new antibiotic produced by the fermentation of an antibiotic A16884-producing strain of *Streptomyces lipmanii*. The salts of A16884 are readily obtained by reaction of A16884 with a suitable acid or base. Antibiotic A16884 and its salts exhibit antibacterial and anthelmintic activity. The antibacterial activity is exhibited against both gram-negative and gram-positive organisms, as well as against plant-pathogenic organisms.

DESCRIPTION OF PREFERRED EMBODIMENTS

Antibiotic A16884, a sulfur-containing peptide antibiotic, is an amphoteric molecule produced by cultivating under controlled conditions a hitherto undescribed strain of *Streptomyces lipmanii* NRRL 3584.

As is the case with many antibiotic-producing cultures, fermentation of an antibiotic A16884-producing strain of *Streptomyces lipmanii* results in the production of a number of antibiotic substances. Antibiotic A16884 is one of these substances. Other substances are either relatively unstable or are present in only very minor quantities.

Antibiotic A16884 can be utilized as such or as a salt, for example, an acid addition salt or a salt with a cation. In the instance of a salt with a cation, the salt can be either a mono or di salt. It is often preferred to prepare salts directly in the purification process so that the antibiotic as separated is in salt form. Antibiotic A16884 has been separated in this manner, and for that reason, is hereinbelow characterized as the monoammonium salt.

The monoammonium salt of antibiotic A16884 is a white, amorphous solid, decomposing at about 180° C., very soluble in water, soluble in dimethylsulfoxide (DMSO), slightly soluble in lower alkanols, and essentially insoluble in acetonitrile and other organic solvents. The specific optical rotation $[\alpha]_D^{25}$ of the monoammonium salt of antibiotic A16884, dried at room temperature in vacuo over anhydrous calcium chloride for about 15 hours, was found to be +140.9° (C = 1 percent, w./v. in water).

Electrometric titration of the monoammonium salt of antibiotic A16884 in a 66 percent dimethyl formamide-water solution at an initial pH of 6.6 revealed the presence of four titratable groups: $pK'a_1 = 3.5$; $pK'a_2 = 5.2$; and $pK'a_3 = 9.2$; and $pK'a_4 = 10.3$. On like titration of a later sample, except at an initial pH of 5.8, the respective values were $pK'a_1 = 3.9$; $pK'a_2 = 5.3$; $pK'a_3 = 9.2$; and $pK'a_4 = 10.5$. When the monoammonium salt of antibiotic A16884 is converted to the acid form, the pK'a at 9.2 disappears. The molecular weight of the monoammonium salt calculated from the titration data is about 435.

Elemental analysis of the monoammonium salt of A16884, dried in vacuo at about 80° C. over phosphorus pentoxide, gave the following values:

| Element | Percent |
| --- | --- |
| Carbon | 44.01 |
| Hydrogen | 5.73 |
| Nitrogen | 10.65 |
| Oxygen | 31.27 |
| Sulfur | 6.86 |

Analysis shows a methoxyl content of 6.64 percent, and an acetyl content of 9.23 percent; and a Van Slyke test for amino nitrogen shows 5.09 percent.

The infrared absorption spectrum of the monoammonium salt of antibiotic A16884 in a mineral oil mull is shown in FIG. 1 of the accompanying drawing. The distinguishable bands in the infrared spectrum over the range of 2.0 to 15.0 microns are as follows: 3.18 (broad band), 5.66, 6.26, 6.57, 6.89, 7.15, 7.28, 7.40, 7.73, 8.00, 8.14, 8.79, 9.24, 9.65, 9.79, and 10.4 microns.

The ultraviolet absorption spectrum of the monoammonium salt of antibiotic A16884 in aqueous solution shows absorption maxima at 242 ($E_{1\,cm}^{1\%} = 126$) and at 265 m$\mu$ ($E_{1\,cm}^{1\%} = 158$); circular dichroism was also measured in aqueous solution and showed a positive Cotton effect at 263 m$\mu$ and a negative Cotton effect at 236 m$\mu$.

Paper chromatography of the monoammonium salt of antibiotic A16884 on Whatman No. 1 paper gave an $R_f$ value of 0.79 in a solvent system of propanol, acetonitrile, and water in a volume ratio of 1:1:1. Bioautographs were obtained by placing the paper chromatograph on agar plates seeded with sensitive organisms, such as *Salmonella gallinarum*, as test organisms.

The NMR spectrum of A16884 in D$_2$O showed the following characteristics: 5.16 ppm. (1H, singlet); 4.86, 4.68 ppm. (2H, AB quartet, J = 12.5 Hz); 3.9–3.7 ppm. (1H, multiplet); 3.67, 3.29 ppm. (2H, AB quartet, J = 18 Hz); 3.53 ppm. (3H, singlet); 2.6–2.3 (2H, multiplet); 2.10 ppm. (3H, singlet); 2.1–1.6 ppm. (4H, multiplet).

Paper chromatography of the monoammonium salt was also carried out in other solvent systems with the following results:

| Solvent System | $R_f$ value |
| --- | --- |
| Ethanol:water (80:20) with 1.5% sodium chloride, paper impregnated with 1N sodium sulfate | .58 |
| Methanol:propanol:water (6:2:1), paper buffered with 0.75 M potassium phosphate, pH 4.0 | .21 |
| Propanol:pyridine:acetic acid:acetonitrile:water (45:30:9:40:36) | .40 |
| tert-Amyl alcohol:acetone:water (2:1:2) | .40 |
| Ethyl acetate:acetic acid:water (3:1:1) | .36 |
| Methyl ethyl ketone:water (92:8), paper buffered with 0.1 N sodium acetate, pH 4.6 | immobile |
| Propanol:water (70:30) | .30 |
| Butanol saturated with water | immobile |
| Butanol saturated with water plus 2% p-toluenesulfonic acid | .60 |

When the monoammonium salt of A16884 is subjected to thin-layer chromatography on silica gel plates in 70 percent aqueous acetonitrile, utilizing a ninhydrin spray as a detector, it has an $R_f$ value of about 0.47; on cellulose plates in 70 percent aqueous acetonitrile, utilizing the same procedure for detection, it has an $R_f$ value of 0.45.

Amino acid analysis of an acid hydrolysate of antibiotic A16884, run by the Spackman-Moore-Stein technique, showed two ninhydrin reacting peaks, one of which was eluted identically with glycine (0.758 μmoles/mg.), the other of which was eluted just prior to glycine and was identified as α-aminoadipic acid (2.39 μmoles/mg.). On like analysis of a later sample, the value observed were 0.49 μmoles/mg. and 1.2 μmoles/mg., respectively.

A number of qualitative chemical tests have been carried out with the antibiotic A16884. Antibiotic A16884 gives a positive test with ninhydrin, Pan Dutscher, Benedict, Molisch, iodine and dansyl chloride reagents, but not with Fehling, ferric chloride, biuret, and Sakaguchi reagents.

The monoammonium salt of antibiotic A16884 is stable at pH 3-9 at 5° C. for 8 days; relatively stable at pH 3-9 at 25° C. for 4 days; and unstable at varying pH values at 100° C. within 5 minutes. Biological activity is slowly lost at pH 3-9 at a temperature of 37° C., half being lost at 4 days.

Based on the various foregoing physical characteristics, the structure of antibiotic A16884 has been determined to be as follows:

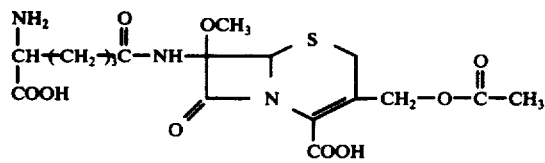

which structure is designated 7-(5-amino-5-carboxyvaleramido)-7-methoxycephalosporanic acid.

Antibiotic A16884 has an inhibitory action against the growth of both gram-positive and gram-negative bacteria. The levels at which partially purified monoammonium salt of antibiotic A16884 shows inhibition against the growth of illustrative organisms are set forth in Table I. The inhibitory levels were determined by the agar-dilution test or by the broth-dilution test (identified in the table by the letters "ad" and "bd", respectively).

In the agar-dilution test, the test organism was streaked on a series of agar plates containing various concentrations of the monoammonium salt of antibiotic A16884 to determine the minimum concentration in mcg./ml. (micrograms per milliliter) in the agar substrate which inhibited the growth of the organism over a period of forty-eight hours (seventy-two hours in the case of the plant pathogen organisms).

In the broth-dilution test, a series of tubes containing nutrient broth containing varied concentrations of the ammonium salt of antibiotic A16884 were inoculated with the test organism to determine the minimum concentration of the monoammonium salt of A16884 in mcg./ml. in the broth substrate which inhibited organism growth for a period of about 20 hours.

TABLE I

| Test Organism | Inhibitory Concentration mcg./ml. |
|---|---|
| Escherichia coli EC 0127 | 6.25 a.d. |
| Proteus PR6 | 1.56 a.d. |
| Proteus PR4 | 3.12 a.d. |
| Salmonella typhimurium 54 | 3.12 a.d. |
| Salmonella typhosa T63 | 1.56 a.d. |
| Staphylococcus aureus 3055 | 50.00 a.d. |
| Staphylococcus aureus 3150 | >50.00 a.d. |
| Pseudomonas aeruginosa X239 | >50.00 a.d. |
| Salmonella flexneri SH3 | 6.25 a.d. |
| Klebsiella aerobacter K1 | 6.25 a.d. |

TABLE I-continued

| Test Organism | Inhibitory Concentration mcg./ml. |
|---|---|
| Klebsiella aerobacter KA14 | 1.56 a.d. |
| Mycobacterium avium X85 | >50.00 a.d. |
| Streptococcus pyogenes C203 | 3.12 a.d. |
| Bacillus subtilis X12.1 | 3.12 a.d. |
| Neurospora sp. M45-846 | >50.00 a.d. |
| Sarcina lutea X186 | 6.25 a.d. |
| Escherichia coli EC0127 | 7.80 b.d. |
| Klebsiella aerobacter KA14 | 15.60 b.d. |
| Salmonella typhosa SA12 | 31.20 b.d. |

No binding by horse serum was noted in any of the above tests.

As can be seen from the above table, antibiotic A16884 as the monoammonium salt exhibits activity against gram-positive and gram-negative bacterial organisms.

More highly purified monoammonium salt of antibiotic A16884 was further evaluated for antibacterial activity in a test employing the broth dilution technique described above. The results, expressed in terms of the minimum number of micrograms per milliliter required to obtain inhibition, were as set forth below in Table II.

TABLE II

| Organism | 12-hour reading | 24-hour reading |
|---|---|---|
| Streptococcus pyogenes C203 | 64 | 128 |
| Staphylococcus aureus 3055 | 128 | >128 |
| Escherichia coli EC14 | 8 | 8 |
| Klebsiella aerobacter sp KA14 | 8 | 16 |
| Proteus sp. PR6 | ND* | 8 |
| Proteus sp. PR17 | 2 | 8 |
| Salmonella typhosa SA12 | ND* | 4 |
| Salmonella typhimurium S4 | ND* | 4 |
| Pasteurella multocida P3 | ND* | 2 |
| Shigella sonnia I SH10 | ND* | 16 |

*ND - Not done.

Antibiotic A16884 and its salts also exhibit in vivo activity against a number of the above organisms and hence are useful in controlling infections caused by such organisms in host animals. Partially purified antibiotic A16884 as the monoammonium salt exhibited an $ED_{50}$ of 23 mg./kg. in mice infected with Proteus PR6, and an $ED_{50}$ of 33.8 mg./kg. in mice infected with Shigella SH3; more highly purified A16884 as the monoammonium salt exhibited an $ED_{50}$ of 3.64 mg./kg. in mice infected with Escherichia coli EC14, an $ED_{50}$ of 23 mg./kg. in mice infected with Salmonella typhosa SA12, and an $ED_{50}$ of 93.4 mg./kg. in mice infected with Klebsiella pneumoniae K1. Administration was by the subcutaneous route.

As noted hereinabove, antibiotic A16884 and its salts exhibit anthelmintic activity in addition to antibacterial activity. Hence antibiotic A16884 or the salt thereof can be administered to warm-blooded animals to control various internal parasites, particularly stomach and intestinal worms such as Ascaris lumbricoides var. suum, Nematospiroides dubius, Aspiculuris tetraptera, Syphacia obvelata, and the like. The administration is preferably by the oral route, for example, by inclusion of antibiotic A16884 or a salt in animal feed, by administration of tables, drenches, etc. containing A16884 or a salt, or by other means. In general, doses of from 1 to 500 milligrams per kilogram or more of animal body weight are effective in single dose administration. Where antibiotic A16884 or a salt thereof is supplied as a constituent of a regular feed, concentrations of from 0.0001 to 0.05 percent or more give good results. A preferred range of concentration of antibiotic A16884 or a salt thereof in feeds is from 0.01 to 0.05 percent.

The anthelmintic activity of antibiotic A16884 is illustrated by the following evaluations.

In a first evaluation, antibiotic A16884 monoammonium salt was administered in a single dose by gavage to each of two mice infected with *Aspiculuris tetraptera* and *Syphacia oblevata* (pinworms). The dose was 500 milligrams of antibiotic A16884 monoammonium salt per kilogram of individual animal body weight, administered in a suspension of physiological saline containing 0.125 percent of methylcellulose as suspending agent. A control group of mice infected with *Aspiculuris tetraptera and Syphacia obvelata* was employed in the evaluation. Both groups were maintained under normal laboratory conditions for 48 hours, following the dosing of the treated group. All mice were then sacrificed and examined to determine the presence and number of pinworms, which were as reported in the following table:

TABLE III

| | Number of Pinworms Per Animal | |
| --- | --- | --- |
| | *Aspiculuris tetraptera* | *Syphacia obvelata* |
| Control | 26 | 52 |
| Antibiotic A16884 monoammonium salt at 500 mg./kg. | 0 | 2.5 |

In another evaluation, antibiotic A16884 monoammonium salt was mixed with standard mouse feed to obtain a plurality of treated feeds, contaiing antibiotic A16884 monoammonium salt in concentrations of 0.005, 0.01, and 0.05 percent by weight. The feeds were utilized as diets for separate groups of mice, five mice per group. About 24 hours after initiation of the feeding, the mice were infected with *Ascaris lumbricoides* var. suum ova. Another group of five mice was fed the non-medicated feed to serve as a control but was similarly infected at the same time with *Ascaris lumbricoides* var. suum. All groups were fed their respective feed and maintained under normal laboratory conditions for a period of ten days, at which time, all mice were taken off feed. On the eleventh day, all mice were sacrificed and the lungs examined to determine the presence and, if present, numbers of lesions of *Ascaris lumbricoides* var. suum.

The level of antibiotic A16884 monoammonium salt in the diet and the average number of lung lesions per animal in each group are set forth in the following table:

TABLE IV

| Group | Average Number of Lung Lesions Per Group |
| --- | --- |
| Control | 2.2 |

TABLE IV-continued

| Group | Average Number of Lung Lesions Per Group |
| --- | --- |
| Antibiotic A16884 monoammonium salt at 0.005 percent | 0.5 |
| Antibiotic A16884 monoammonium salt at 0.01 percent | 0.4 |
| Antibiotic A16884 monoammonium salt at 0.05 percent | 0.4 |

Antibiotic A16884 can be produced by cultivating a newly found and hitherto undescribed organism strain isolated from soil samples obtained from South America.

The organism was isolated from the above soil samples by suspending portions of the soil samples in sterile distilled water, and by streaking the suspensions on nutrient agar. The seeded nutrient agar plates were incubated at about 25°–35° C. for several days. At the end of the incubation period, colonies of the antibiotic A16884-producing organism were transferred with a sterile platinum loop to agar slants. The agar slants were then incubated to provide suitable amounts of inoculum for the production of antitiotic A16884.

The actinomycete used according to this invention for the production of antibiotic A16884 has been designated as a strain of *Streptomyces lipmanii* Waksman and Curtis.

The novel organism capable of producing antibiotic A16884 has been placed on permanent deposit without restriction as to availability with the culture collection of the Northern Utilization Research and Development Division, Agricultural Research Service, U.S. Department of Agriculture (Formerly Northern Regional Research Laboratories), Peoria, Illinois 61604, and is available to the public under culture No. NRRL 3584.

The characteristics of *Streptomyces lipmanii* NRRL 3584 are given in the following tables. The methods recommended for the International Streptomyces Project (Shirling et al., "Methods for Characterization of Streptomyces Species," *Intern. Bull. Systematic Bacteriol.* 16: 313–340 [1966]) for the characterization of Streptomyces species have been used along with certain supplementary tests. Color names were assigned according to the ISCC-NBS method described by Kelly et al. in *The ISCC-NBS Method of Designating Colors and a Dictionary of Color Names* (U.S. Department of Commerce Circ. 553, Washington, D.C. 1955). Figures in parenthesis refer to the Tresner and Backus color series (Tresner et al., "System of Color Wheels for Streptomyces Taxonomy," *Appl. Microbiol.* 11: 335–338 [1963]) and color tab designations are underlined. The Maerz and Paul color blocks (Marez et al., *Dictionary of Color* (McGraw-Hill Book Co., Inc., New York, 1950) are enclosed in bracket Cultures were grown at 30° C. for 14 days unless noted otherwise.

TABLE V

| Property Observed | Characteristics of A16884 |
| --- | --- |
| Morphology | Sporophores are usually straight to flexuous with occasional hooks produced; spores are short, cylindrical; 0.5–1.5μ × 1.0–2.5μ, and occur usually in chains of 3–10 and occasionally from 10–50. Spores are smooth in outline as observed by electron microscopy. |
| Culture Characteristics on: | |
| ISP No. 2 (Yeast-Malt Extract Agar) | Growth moderate, reverse dark grayish brown [8H9]; aerial mycelium pale yellow (Y) 2db |
| ISP No. 3 (Oatmeal Agar) | Growth moderate, reverse dark |

TABLE V-continued

| Property Observed | Characteristics of A16884 |
|---|---|
| | grayish yellow [13E4]; aerial mycelium moderate, white (W) 13ba to pale yellow (Y) 2db. |
| ISP No. 4 (Inorganic salts and Soluble Starch Agar) | Growth moderate, reverse brownish gray [7C7]; aerial mycelium moderate, pale yellow (Y) adb. |
| ISP No. 5 (Glycerol - Asparagine Agar) | Growth abundant, reverse light yellowish brown [13I7]; aerial mycelium abundant, grayish yellowish pink (R) 5dc. |
| Tomato paste-oatmeal Agar | Growth abundant, reverse grayish yellowish brown [15E8]; aerial mycelium abundant, yellowish gray (GY) 2dc. |
| Emersons' Agar | Growth moderate, reverse dark grayish yellowish brown [8E9]; aerial mycelium and spores absent |
| Bennetts' Agar | Growth abundant, reverse medium yellowish brown [14E7]; aerial mycelium abundant, grayish yellow (R) 3ec. |
| Czapeks' Agar | Growth scant, white; scant aerial mycelium (W) 13ba. |
| Glucose-asparagine Agar | Growth abundant, reverse grayish yellow [12D4]; aerial mycelium abundant, yellowish gray (GY) 2dc. |
| Tyrosine Agar | Growth moderate, reverse light yellowish brown [12C5]; aerial mycelium abundant, grayish yellow (R) 3ec. |
| Nutrient Agar | Moderate growth, reverse pale yellow [11C1]; no aerial mycelium. |
| Calcium Malate Agar | Moderate growth, reverse black [56C1]; very scant aerial mycelium. |
| Physiology | |
| Action on milk | Coagulation, peptonization. |
| Nitrate reduction | Positive |
| Melanin production | |
| Peptone-iron agar | Negative |
| Tryptone-yeast ext. broth | Negative |
| Temperature requirements on tomato paste-oatmeal agar | Abundant growth and sporulation at 26° C. and 30° C; slight growth at 37° C; no growth at 43° C. |
| Response of vegetative color to pH change | |
| 0.05N HCl | Brownish-gray pigment changes to red. |
| 0.05N NaOH | No change. |
| Gelatin liquefaction | 100% |

In Table VI are set forth the results of carbon utilization tests carried out on organism NRRL 3584. In the table, the following symbols are employed:

TABLE VI

| Carbon Utilization Pattern for NRRL 3584 | |
|---|---|
| Compound | Growth Response |
| L-arabinose | − |
| sucrose | − |
| D-xylose | + |
| D-fructose | − |
| glucose | + |
| rhamnose | − |
| raffinose | − |
| i-inositol | − |
| D-mannitol | − |
| Control (no carbon) | − |

+ = growth and utilization
− = no growth, no utilization

As noted above, antibiotic A16884 can be produced by the cultivation of NRRL 3584. The culture medium employed in producing antibiotic A16884 by cultivation of the above-identified organism can be any one of several media, since, as is apparent from the above-described utilization tests, the organism is capable of utilizing different energy sources. However, for economy of production, maximum yield of antibiotic, and ease of isolation of the antibiotic, certain relatively simple nutrient sources are preferable. For example, the media which are useful in the production of the antibiotic include an assimilable source of carbon such as glucose, starch, glycerine, molasses, dextrin, and the like. The preferred source of carbon is glucose. Additionally, employable media include a source of assimilable nitrogen such as soybean meal, corn steep solids, yeast, cottonseed meal, beef extract, peptones (meat or soy), casein, amino acid mixtures, and the like. Preferred sources of nitrogen are peptones, soybean meal, amino acid mixtures, and the like. Among the nutrient inorganic salts which can be incorporated in the culture media are the customary salts capable of yielding sodium, potassium, ammonium, calcium, phosphate, sulfate, chloride, carbonate, and like ions.

Minor elements necessary for optimum growth and development of the organism used for the production of antibiotic A16884 can also be included in the culture medium. Such trace elements commonly occur as impurities in the other constituents of the medium in amounts sufficient to meet the growth requirements of the actinomycete employed in this invention.

The initial pH of the culture medium can be varied. However, it has been found desirable that the initial pH of the medium be between 6.5 and 7.2. As has been observed with other actinomycetes, the pH of the medium gradually increases throughout the growth period of the organism while the antibiotic is being produced, and may attain a level of from 6.7 to 7.5 or above, the final pH being dependent at least in part on the initial pH of the medium, the buffers present in the medium, and the period of time the organism is permitted to grow.

Submerged, aerobic cultural conditions are the conditions of choice for the production of antibiotic A16884. For preparation of relatively small amounts, shake flask and surface culture in bottles can be employed; but for the preparation of large amounts, submerged aerobic culture in sterile tanks is preferred. The medium in the sterile tank can be inoculated with a sporulated suspension; but because of the growth lag experienced when a sporulated suspension is used as the inoculum, the vegetative form of the culture is preferred. By thus avoiding the growth lag, more efficient use of the fermentation equipment is realized. Accordingly, it is desirable first to produce a vegetative inoculum of the organism by inoculating a relatively small quantity of culture medium with the spore form of the organism; and when a young, active vegetative inoculum has been obtained, to transfer the vegetative inoculum aseptically to the large tank. The medium in which the vegetative inoculum is produced can be either the same as or different from the medium utilized for the large-scale production of antibiotic A16884.

The organism which produces antibiotic A16884 will grow over a wide temperature range between 25°–37° C. Optimal production of A16884 seems to occur at temperatures of 26°–30° C. In general, maximum production of the antibiotic occurs within about 36–72 hours after inoculation of the culture medium.

As is customary in aerobic, submerged culture processes, sterile air is blown through the culture medium. For efficient growth of the organism and antibiotic A16884 production, the volume of air employed in the tank production of A16884 is from 0.2 to 0.4 volume of air per minute per volume of culture. The preferred volume is 0.40 volume of air per minute per volume of culture medium.

The concentration of antibiotic activity in the culture medium can be followed readily during the fermentation period by testing samples of the culture medium for their inhibitory activity against the growth or organisms known to be inhibited by the presence of antibiotic A16884. The organisms *Sarcina lutea* and *Salmonella gallinarum* have been found to be useful for this purpose. The testing of the samples can be carried out by the well-known turbido-metric or diso-plate methods.

In general, maximum production of A16884 occurs within one to three days after inoculation of the culture medium is submerged aerobic culture or shake flask culture processes.

The antibiotic activity produced during the fermentation of A16884 occurs in the antibiotic broth. Accordingly, isolation techniques employed in the production of A16884 are designed to permit maximum recovery of the antibiotic from the broth. Thus, for example, mycelium and undissolved solids are removed from the fermentation broth by conventional means such as filtration or centrifugation, and antibiotic A16884 can be recovered from the filtered or centrifuged broth by employing extraction or adsorption technique.

For the recovery of A16884 by adsorption techniques, various adsorbents and ion exchange resins can be used, for example, carbon, silica gel, alumina, and ion exchange resins. Antibiotic A16884 as obtained from fermentation may be in either amphoteric or salt form, depending upon fermentation conditions. Regardless of which form, it can be adsorbed onto one of the above or similar adsorbents from solution in a suitable solvent. The adsorbed antibiotic A16884 or salt can then be eluted from the adsorbent by suitable elution techniques, such as by washing the adsorbent on which the antibiotic A16884 or salt thereof is adsorbed with a solvent. Where the elution is carried out by washing with a solution of, e.g., ammonium formate or sodium acetate, the process results in elution of antibiotic A16884 as the ammonium or sodium salt, respectively. Such salts are readily converted back to antibiotic A16884 in conventional procedures. In the foregoing recovery procedure, microcrystalline cellulose can also be used as adsorbent.

Salts of antibiotic A16884 other than ammonium or alkali metal are preferably prepared by conventional reaction of antibiotic A16884 in unmodified amphoteric form with the respective acid or base. Thus, in preparing acid addition salts, antibiotic A16884 is reacted with an inorganic or organic acid. Representative suitable acids include hydrochloric acid, hydrobromic acid, hydroiodic acid, sulfuric acid, phosphoric acid, acetic acid, benzoic acid, sulfamic acid, tartaric acid, citric acid, maleic acid, succinic acid, ascorbic acid, and glycolic acid.

Antibiotic A16884 also forms salts with cations by reaction of A16884 in unmodified, amphoteric form with inorganic and organic bases and salts. Exemplary of these salts are ammonium and substituted ammonium salts; alkali metal salts, such as sodium potassium, lithium, cesium, and rubidium; alkaline earth metal salts such as calcium, strontium, and barium; and salts with other metals such as aluminum, copper, zinc, magnesium, and silver. In respect to organic bases, the identify of the base is not critical, although, in general, a base having a pH of, numerically, 3.0 or above in water is preferred. Representative suitable organic bases include benzylamine, methylamine, diethylamine, triethylamine, procaine, diisopropylamine, ethanolamine, cyclohexylamine, dicyclohexylamine, diphenylamine, di-n-butylamine, quinoline, and pyridylamine.

The salts of antibiotic A16884 which are pharmaceutically acceptable are generally preferred. However, all salts are useful as intermediates in the production, separation, and purification of antibiotic A16884. For therapeutic purposes, either cationic or anionic pharmaceutically acceptable salts are generally equivalent to antibiotic A16884; however, particular salts are occasionally preferred due to a favorable property, such as solubility, conferred by the salt-forming moiety.

In order to illustrate more fully the operation of the invention, the following examples are provided by way of illustration.

EXAMPLE 1

SHAKE FLASK PRODUCTION OF ANTIBIOTIC A16884

A sporulated culture of *Streptomyces lipmanii* NRRL 3584 was produced by growing the organism on a nutrient agar slant having the following composition:

| | |
|---|---|
| Dextrin | 10.00 g. |
| Yeast Extract | 1.00 g. |
| Hydrolyzed Casein ("N-Z Amine-Type A," Sheffield Chemical Company) | 2.00 g. |
| Beef Extract | 1.00 g. |
| Meer Agar (washed three times) | 20.00 g. |
| Deionized water | 1 liter |

The pH of the medium was adjusted to pH 7.0 by the addition of sodium hydroxide.

The agar slant was inoculated with spores of *Streptomyces lipmanii* NRRL 3584 and was incubated for 6 days at 30° C. The agar slant was then covered with sterile distilled water and gently scraped to remove the spores and cells in an aqueous suspension thereof. One milliliter of the resulting suspension was used to inoculate each 100 ml. portion of a vegetative medium having the following composition:

| Glucose | 15.00 g. |
|---|---|
| Soybean meal | 15.00 g. |
| Cornsteep solids | 5.00 g. |
| Calcium carbonate | 2.00 g. |
| Sodium chloride | 5.00 g. |
| Deionized water | 1 liter |

The pH of the vegetative medium was adjusted to pH 6.7 by the addition of sodium hydroxide.

The vegetative inoculum was shaken for 36 hous at 30° C on a reciprocal shaker with a two-inch stroke at 108 rpm. The inoculum so prepared was then utilized in the production of A16884 as follows:

A production medium was prepared having the following composition:

| Soybean meal | 15.00 g. |
|---|---|
| Casein | 1.00 g. |
| Sodium nitrate | 3.00 g. |
| Glucose syrup (50 percent glucose) | 20.00 g. |
| Tap water | 1 liter |

One hundred milliliter portions of the production medium were placed in 500 milliliter Erlenmeyer flasks which were sterilized at 120° C. for 30 minutes. When cooled, each flask was inoculated with a five percent vegetative inoculum. The fermentation was shaken for 72 hours at 30° C. on a rotary shaker operating at 250 rpm. During the fermentation, the medium was aerated with sterile air at a rate of 0.4 v./v./min. Isolation was carried out essentially as reported hereinbelow in Example 8.

EXAMPLE 2

Antibiotic A16884 was produced according to the process of Example 1, but utilizing a production medium having the following composition:

| Distillers' solubles (Nadrisol) | 5.00 g. |
|---|---|
| Soybean flour (Nutrisoy 200D) | 5.00 g. |
| Peanut meal | 5.00 g. |
| Blackstrap molasses | 5.00 g. |
| Oatmeal | 5.00 g. |
| Glycerol | 10.00 g. |
| Tap water | 1 liter | and utilizing instead of a rotary shaker a reciprocal shaker operating at 108 strokes per minute.

EXAMPLE 3

Antibiotic A16884 was produced according to the process of Example 1, but utilizing a production medium having the following composition:

| Oatmeal | 20.00 g. |
|---|---|
| Glycerol | 10.00 g. |
| Tap water | 1 liter |

EXAMPLE 4

Antibiotic A16884 was produced according to the process of Example 1, but utilizing a production medium having the following composition:

| Cottonseed flour | 20.00 g. |
|---|---|
| Glycerol | 10.00 g. |
| Glucose | 5.00 g. |
| Tap water | 1 liter |

EXAMPLE 5

Antibiotic A16884 was produced according to the process of Example 1 but utilizing a production medium having the following composition:

| Glucose | 20.00 g. |
|---|---|
| Soluble starch | 10.00 g. |
| Peptone (Wilson's 159) | 30.00 g. |
| Hydrolyzed casein ("N-Z amine-type A," Sheffield Chemical Co.) | 4.00 g. |
| Magnesium sulfate heptahydrate | 5.00 g. |
| Sodium carbonate | 2.00 g. |
| Tap water | 1100 ml. |

EXAMPLE 6

Another sporulated culture of Streptomyces lipamanii NRRL 3584 was produced by growing the organism on a nutrient agar slant. The slant in this instance had the following composition:

| Dextrin | 10.00 g. |
|---|---|
| Cottonseed flour | 10.00 g. |
| Yeast extract | 1.00 g. |
| Meer agar | 25.00 g. |
| Deionized water | 1000 ml. |

The pH of the medium was adjusted, by addition of sodium hydroxide to 7.0.

The agar slant was inoculated with spores of *Streptomyces lipamanii* NRRL 3584 and incubated for 7 days at 30° C. The agar slants were then scraped to remove spores to which were added 20 ml. of sterile beef serum. To a sterile lyophile tube was then transferred 0.1 ml. of the resulting serum spore suspension; it was freeze-dried in the form of pellets.

The freeze-dried pellets thus obtained were used to inoculate a vegetative medium having the following composition:

| Glucose | 5.00 g. |
|---|---|
| Dextrin | 10.00 g. |
| Bacto-tryptone | 5.00 g. |
| Yeast extract | 5.00 g. |
| Magnesium sulfate heptahydrate | 2.00 g. |
| Deionized water | 1 liter |

The pH of the medium was 6.7 and was left unadjusted.

EXAMPLE 7

PILOT PLANT PRODUCTION OF ANTIBIOTIC A16884

To a 40-liter stainless steel fermentor were added 24 liters of a medium having the following composition:

| | |
|---|---|
| Antifoam A (an anti-foaming agent sold by Dow Corning) | 0.20 g. |
| Glucose | 5.00 g. |
| Dextrin 700 | 50.00 g. |
| Soybean grits | 25.00 g. |
| Molasses, blackstrap | 3.00 g. |
| Potassium biphosphate | 0.25 g. |
| Calcium carbonate | 2.50 g. |
| Cold tap water | to 25 liters |

The initial pH was 6.5 and was not adjusted. The medium was sterilized for 30 minutes at 120° C., cooled, and then inoculated with a five percent vegetative inoculum produced as in Example 6. The fermentation was carried out at 30° C. for 66 hours, aerated with sterile air at the rate of 0.35 v./v./min., and agitated by a mechanical stirrer operated at 420 revolutions per minute. The terminal pH was 7.5.

A16884 was recovered from the broth following the isolation procedure set forth in Example 8.

EXAMPLE 8

ISOLATION OF CRUDE ANTIBIOTIC A16884 AS THE MONOAMMONIUM SALT

Approximately 60 liters of broth obtained as reported in Example 7 was filtered with the aid of Hyflo Supercel (a diatomaceous earth solid by Johns-Manville Products Corporation). The broth filtrate was passed over a 9.6 × 150 cm. column packed with carbon (Pittsburgh Cal. 12 × 40, sold by Pittsburgh Activated Carbon Co.). The column was washed with water until the effluent was colorless, and the activity adsorbed on the carbon was removed by passing 50 percent aqueous acetone over the column. The fractions containing the activity were combined, concentrated in vacuo to remove acetone, and applied to a 5.9 × 104 cm. column packed with IRA-68 resin (formate cycle) (an anion exchange resin sold by Rohm and Haas Co. and subsequently washed with formic acid to convert the resin to the formate cycle). The column was washed with water until the effluent was clear and colorless, and the activity was removed by washing with 0.1M ammonium formate solution. The active fractions were combined, and passed over a 4.3 × 72 cm. carbon (Pittsburgh 12 × 40) column. The column was washed with six column volumes of water, and the activity was eluted with 30 percent aqueous acetonitrile. The active fractions were combined, concentrated in vacuo to remove acetonitrile, and freeze dried. The yield was 25-30 grams of solids.

The freeze-dried preparation was dissolved in a minimum of water and applied to a 7.2 × 60 cm. column packed with a microcrystalline cellulose product (Avicel, sold by FMC Corporation), suspended in 70 percent aqueous acetonitrile, and washed with acetonitrile prior to addition of the active sample. After application of the sample, the column was washed with one column volume of acetonitrile, and the activity was eluted with methanol. The active fractions were combined and concentrated by approximately 200 milliliters, and the activity was precipitated by the addition of 10 volumes of acetone. The precipitate was filtered, washed with acetone, and dried in vacuo. The yield was 9-12 g.

Twenty grams of material obtained as described above was dissolved in a minimum of water and applied to a silical gel column (7.2 × 60 cm.). The silica gel (Grade 950 produced by Davison Chemical) was previously washed with water, then methanol, and suspended in 70 percent acetonitrile for packing the column. After application of the sample, the column was washed with one column volume of acetonitrile, and the activity was eluted with 70 percent acetonitrile. The most active fractions were combined, concentrated to dryness in vacuo, and dissolved in methanol, and the activity was precipitated with 10 volumes of acetone. The precipitate was filtered, washed with acetone, and dried in vacuo. The yield was 8 g. Less active fractions yielded an additional 6 grams.

EXAMPLE 9

PURIFICATION OF A16884 MONOAMMONIUM SALT

One gram of a freeze-dried preparation prepared as described in Example 8 was dissolved in four milliliters of water and applied to a 2 × 60 cm. column packed with 175 milliliters of silica gel Grade 950 in 80 percent aqueous acetonitrile. The column was eluted with acetonitrile:water (4:1). The elution was followed by assay and paper chromatography. As a result of the elution, a plurality of fractions was obtained. The fractions containing antibiotic A16884 as the monoammonium salt were combined, concentrated to dryness, dissolved in a small volume of dimethylsulfoxide, then in several milliliters of ethanol, and the activity was precipitated with the addition of excess ether. The precipitate was centrifuged and dried in vacuo. The yield of antibiotic A16884 monoammonium salt was 91 mg.

EXAMPLE 10

PREPARATION OF ANTIBIOTIC A16884 IN ACID FORM

Two hundred milligrams of the monoammonium salt of A16884 were dissolved in 30 milliliters of water, and 6 milliliters of Dowex 50 × 12(H+) resin (sold by the Dow Chemical Co.) were added. The mixture was stirred for thirty minutes, filtered, the resin washed with water on the filter, and the filtrates were combined. The combined filtrate had a pH of 2.7. The filtrate was concentrated in vacuo to about 1 milliliters, 4 milliliters of methanol were added, and the acid was precipitated by the addition of 40 milliliters acetone. The precipitate was removed by centrifugation and dried in vacuo yielding 35 milligrams of antibiotic A16884 in the acid form. It exhibited pK'a's of 3.9, 5.2, and 10.5 when titrated in 66 percent dimethylformamide at an initial pH of 4.5.

EXAMPLE 11

PREPARATION OF DISODIUM SALT OF A16884

One hundred and eighty milligrams of A16884 monoammonium salt were dissolved in about 2 milliliters water and the pH was adjusted to 10 with 1N NaOH. The solution was concentrated in vacuo to a low volume, 4 milliliters methanol were added, and the disodium salt was precipitated with the addition of 40 milliliters acetone. The salt was removed by centrifugation and dried in vacuo. It exhibited pK'a's of 3.9, 5.2, and 10.5 when titrated in 66 percent dimethylformamide at an initial pH of 10.4; and when analyzed by atomic absorption analysis, it showed 6 percent sodium.

EXAMPLE 12

PREPARATION OF ANTIBIOTIC A16884 HYDROCHLORIDE

A16884 Monoammonium salt (200 mg.) was dissolved in two milliliters of water and adjusted to pH 2.0 with 1N HCl. The reaction mixture was then diluted with 5.0 milliliters of methanol and 50 milliliters of acetone added to precipitate the desired antibiotic A16884 hydrochloride. It was separated by centrifugation, washed with acetone, and dried in vacuo. Analysis showed 5.74 percent chlorine and electrometric titration in 66 percent dimethylformamide at an initial pH of 5.0 showed titratable groups at 3.9, 5.2, and 10.4.

EXAMPLE 13

ISOLATION OF CRUDE ANTIBIOTIC A16844 AS THE MONOSODIUM SALT.

Approximately 60 liters of broth, obtained as reported in Example 7, were filtered with the aid of Hyflo-Supercel. The broth filtrate was passed over a 9.6 × 150 cm. column packed with carbon (Pittsburgh Cal. 12 × 40). The column was washed with water until colorless, and the absorbed activity was removed by passing 50 percent aqueous acetone over the column. The fractions containing the activity were combined, concentrated in vacuo to remove the acetone, and applied to 5.9 × 104 cm. column packed with IRA-68 (acetate cycle). The column was washed with water until the effluent was clear and colorless, and the activity was removed by washing with 0.1M sodium acetate. The active fractions were combined, and passed over a 4.3 × 72 cm. column packed with Pittsburgh Cal. (12 × 40) carbon. The column was packed with six column volumes of water, and the activity was eluted with 30 percent aqueous acetone. The active fractions were combined, concentrated in vacuo to remove the acetone, and freeze dried. Yield of 20–30 g. Analysis showed 2.5 percent sodium.

Antibiotic A16884, as the monoammonium salt, was evaluated for the control of plant-pathogenic bacterial organisms. In this evaluation, antibiotic A16884 monoammonium salts was formulated in an aqueous spray formulation at a concentration of 400 parts thereof per million parts by weight of ultimate composition. Thirty-dayold tomato plants were used in the evaluation, 2 plants/pot. Plants in one pot were treated with the solution, described above, were allowed to air dry, and were then inoculated with a medium sustaining an active growth of *Pseudomonas solanacearum*. The plants in the other pot were sprayed with an aqueous spray solution identical with the treating solution described above but lacking the antibiotic, to serve as a control. The plants serving as control were likewise subsequently inoculated. All plants were held for 24 hours in a moist chamber, then removed and held for 7 days under good agricultural conditions. At the end of this seven-day period all of the plants were observed to determine presence, and if present, degree, of infection. The plants treated with antibiotic A16884 monoammonium salt were completely free of symptoms of disease caused by *Pseudomonas solanacearum*, whereas the control plants exhibited extensive symptoms attributable to *Pseudomonas solanacearum*.

We claim:
1. The compound of the formula

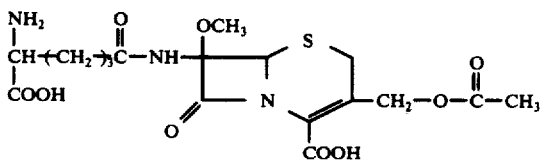

or a salt thereof.

2. A compound having the formula:

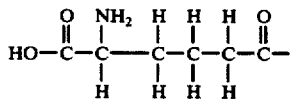

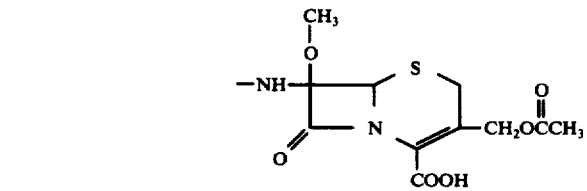

and pharmaceutically acceptable salts thereof.

* * * * *